US012611510B2

(12) United States Patent
Marcoz

(10) Patent No.: US 12,611,510 B2
(45) Date of Patent: Apr. 28, 2026

(54) DOSE CAPTURE ADD-ON DEVICE FOR HANDHELD INJECTION SYRINGE

(71) Applicant: BIOCORP PRODUCTION S.A.S., Issoire (FR)

(72) Inventor: Alain Marcoz, Issoire (FR)

( * ) Notice: Subject to any disclaimer, the term of this patent is extended or adjusted under 35 U.S.C. 154(b) by 698 days.

(21) Appl. No.: 17/997,548

(22) PCT Filed: Apr. 30, 2020

(86) PCT No.: PCT/IB2020/000387
§ 371 (c)(1),
(2) Date: Oct. 30, 2022

(87) PCT Pub. No.: WO2021/220024
PCT Pub. Date: Nov. 4, 2021

(65) Prior Publication Data
US 2023/0330348 A1      Oct. 19, 2023

(51) Int. Cl.
*A61M 5/315*          (2006.01)
(52) U.S. Cl.
CPC ................................ *A61M 5/3158* (2013.01)
(58) Field of Classification Search
CPC ...... A61M 2205/3317; A61M 5/31555; A61M 2205/50; A61M 5/31575; A61M 5/3158
See application file for complete search history.

(56) References Cited

U.S. PATENT DOCUMENTS

| | | | | |
|---|---|---|---|---|
| 5,611,784 A | * | 3/1997 | Barresi | ................. B01L 3/0217 |
| | | | | 604/246 |
| 2015/0352288 A1 | | 12/2015 | Andersen | |
| 2018/0200452 A1 | | 7/2018 | Marcoz et al. | |
| 2018/0207366 A1 | * | 7/2018 | Marcoz | ............. A61M 5/31568 |

FOREIGN PATENT DOCUMENTS

| | | |
|---|---|---|
| JP | 2002503122 A | 1/2002 |
| JP | 2018524140 A | 8/2018 |
| KR | 1020040096533 A | 11/2004 |

(Continued)

OTHER PUBLICATIONS

ISR: European Patent Office; NL Apr. 12, 2020.

*Primary Examiner* — Deanna K Hall
(74) *Attorney, Agent, or Firm* — Patshegen IP; Moshe Pinchas

(57) ABSTRACT

A handheld dose capture device, configured and adapted to be releasably attachable to a handheld injection syringe, comprising: a support body, adapted and configured to releasably engage with an elongated body of the injection syringe in parallel alignment to a central longitudinal axis thereof; a displacement replicator system, adapted and configured to replicate a translational movement of a syringe plunger, in parallel to the longitudinal axis; a coupling means, adapted and configured to couple a proximal extremity of the plunger with a proximal extremity of the displacement replicator system; the dose capture device comprising at least one sensor and a processing system, these being adapted and configured to correlate the translational movement of the displacement replicator system with a selection and/or ejection of a dose of injectable substance operated by a user via translational movement of the plunger along the longitudinal axis.

18 Claims, 4 Drawing Sheets

(56)            References Cited

FOREIGN PATENT DOCUMENTS

| | | | |
|---|---|---|---|
| KR | 1020190135566 | A | 12/2019 |
| WO | 2016040949 | A1 | 3/2016 |
| WO | 2018136901 | A1 | 1/2018 |
| WO | 2019175790 | A1 | 9/2019 |
| WO | 20190175790 | A1 | 9/2019 |

* cited by examiner

DOSE CAPTURE ADD-ON DEVICE FOR HANDHELD INJECTION SYRINGE

The present invention pertains generally to the field of handheld injection syringes, and ways and equipment with which to either capture a dose of injectable substance set by a user of such injection syringes, and/or determine the dose of actually ejected, and/or administered, injectable substance from such a handheld injection syringe.

An example of a system and device that captures a dose administered or ejected by such a handheld injection syringe is described in PCT patent application published as WO2018136901A1. This document discloses a handheld injection syringe for use in a teaching or training system for teaching people how to effect injections. The system includes a hypodermic syringe with needle and plunger, in which the plunger shaft has a helical or substantially helical groove along the longitudinal axis of the plunger shaft. The helical groove is configured to rotate about 270 degree, along a length of about 50 mm to about 100 mm, in other words about 76 mm per 360 degree. A signal processing system is mounted on the finger lugs at a proximal end of the syringe body, and includes a keyed rotary sensor or potentiometer, such as a hollow-shaft type sensor. The rotary sensor has a stationary housing and a bearing. The bearing has a generally D-shaped opening and the opening is configured to slidably accommodate the D-shaped plunger shaft, the bearing rotating along the helical groove of the plunger shaft during linear advancement of the plunger shaft while the housing remains stationary. When the plunger is advanced distally toward the needle tip in a linear movement to deliver medication, the rotary sensor monitors the angular position of the bearing relative to the housing. The rotary sensor calculates a distance of the linear movement based on the amount of rotation of the helical groove measured by the rotary sensor. The amount of rotation of the helical groove, that is, the angular position of the bearing, is determined based on a change of resistance of the rotary sensor due to the rotation of the bearing.

The applicants of the present have noticed that none of existing art solutions, such as the one described above, are sufficiently easy to use, and/or precise, and/or simple to construct, when it comes to determining a dose set, and/or ejected and/or administered, by the user, in handheld injection syringes that contain particularly small volumes, for example, of only several to tens of, millilitres of injectable substance. This is particularly the case for example, in handheld hypodermic injection syringes that contain up to a maximum of 30 millilitres of injectable substance. For example, the previously described technical solution above, even supposing that it would be functional with such small volume handheld injection syringes, requires significant modification of the shape and functioning of the plunger, which significantly renders the overall functioning of the device more complex and requires a whole separate production and assembly line to be provided in order for the required changes in the plunger to be effective.

Accordingly, one object of the present is to provide a device for capturing a dose set by a user for injection, and/or an ejected and/or administered dose, of injectable substance from a handheld injection syringe, which does not require modification of the already existing commercially available handheld injection syringes.

Accordingly, another object of the present is to provide a system and/or method for capturing such a dose set by a user, and/or ejected, and/or administered by said user, of an injectable substance from a handheld injection syringe.

These, and other objects, will become apparent from the description, figures and claims of the present application.

According to one object, therefore, there is provided a handheld dose capture device, configured and adapted to be releasably attachable to a handheld injection syringe comprising an elongated body having a longitudinal bore defining a central longitudinal axis, the elongated body having a proximal extremity and a distal extremity, and a syringe plunger located within, and movable along said central longitudinal axis of said bore, the syringe plunger extending beyond said proximal extremity;

wherein the releasably attachable dose capture device comprises:

a support body, adapted and configured to releasably engage with at least an outer surface of the elongated body of the handheld injection syringe in parallel alignment to the central longitudinal axis of said elongated body;

a displacement replicator system, adapted and configured to replicate a translational movement of the plunger, in parallel to the longitudinal axis;

a coupling means, adapted and configured to couple a proximal extremity of the plunger with a proximal extremity of the displacement replicator system; and wherein the handheld dose capture device comprises at least one sensor and a processing system, and the at least one sensor and processing system are adapted and configured to correlate the translational movement of the displacement replicator system with a selection and/or ejection of a dose of injectable substance operated by a user through the translational movement of the plunger along the longitudinal axis.

The handheld injection syringe as described above is commonly found in trade and commerce and the structure thereof known per se. It should be noted that the add-on device as envisaged herein in the present application does not modify the structure or functioning of such commercially available handheld injection syringes, for example, hypodermic syringes. The handheld syringe generally contains an injectable substance within the central bore of the body of the syringe. However, the possibility is also envisaged by the present application that the syringe on unpackaging contains no injectable substance, and the user then withdraws such a substance into the central longitudinal bore, for example, by moving the plunger in proximal direction when the distal extremity of the syringe body has been connected to a supply container of injectable substance, for example, a vial, or for example, after reconstitution in a separate storage and/or reconstitution device. This kind of usage is also very common in association with handheld injection syringes.

The handheld dose capture device is configured and adapted to be releasably attachable to a handheld injection syringe. By "releasably attachable", "releasably attached", "releasably mounted" and other similar expressions as may be found in the present application, it is to be understood that what is meant is that the dose capture device connects in some temporary manner to the handheld injection syringe that allows it to be easily removed once it has fulfilled its purpose, or say, when the user has expelled or otherwise used up the injectable substance contained in the injection syringe. To such an extent therefore, the dose capture device is both releasable from, and attachable, to, the handheld injection syringe.

The releasably attachable dose capture device comprises a support body, which is adapted and configured to releasably connect, clip onto, or otherwise engage with at least an outer surface of the elongated body of the handheld injection syringe in parallel alignment to the central longitudinal axis of said elongated body.

According to one object, the support body of the dose capture device is releasably attachable to the handheld injection syringe at at least one or more locations along a length of the elongated body of the syringe. For example, the support body can be provided with one or more removable or otherwise activated clips that extend around and engage with an outer surface of the elongated body of the syringe at several locations along the length of the syringe body. For example, one, two, or more clips could be provided which extend outward from the support body and extend around the periphery of the outer surface of the syringe body.

Alternatively, and according to yet another object, the support body advantageously comprises a cradle for releasably contacting at least an outer surface of the elongated body of the handheld injection syringe. The cradle can extend along substantially at least a part, or substantially the whole length of the syringe body, although generally it will only extend along a part of the length of the syringe body to allow for locating of the finger lugs and proximal extremity of the syringe body, the lugs projecting outwardly from the syringe body, and the proximal extremity of such syringe bodies generally having a wider diameter than the rest of the syringe body, and therefore requiring an differently and correspondingly sized cradle fork having an appropriately dimensioned radius of curvature to accept the radius of curvature of the outer surface of the proximal extremity of the syringe body. In general, the cradle is configured with an outwardly projecting concave curved wall, for example, that either substantially matches the radius or curvature of the outer surface of the syringe body, or alternatively is of slightly narrower radius of curvature than the outer surface of the syringe body, and which cradle wall forms a longitudinally oriented hollow or groove, shaped to receive and retain the body of the syringe for the duration of use of the syringe. The cradle wall of the support body is advantageously made of elastically deformable material, such that when the syringe body is pushed against the cradle, it snap-fits, or push-fits into the longitudinally formed groove via elastic deformation of the cradle wall. Once the syringe body is seated within the longitudinal groove, the elastic recall of the cradle wall material forces the cradle wall to engage with and securely hold the outer surface of the syringe body. Similarly, when the syringe is spent, the syringe body can be removed from the cradle by elastically deforming the walls of the cradle once again to ease, or pull force, out the syringe body and free it from the support body.

According to yet another object, the support body comprises a tubular body, having a longitudinal central bore defining a longitudinal axis that is located parallel to the longitudinal axis of the elongated body of the injection syringe when the dose capture device is mounted on the handheld injection syringe. The tubular body and cradle wall are attached one to the other by any appropriate means, but preferably and advantageously, the cradle and tubular body are made of one and the same material, for example, a suitable plastic or polymeric material, for example produced by injection and/or blow moulding. Such a suitable polymeric material can be a polycarbonate (PC)/acrylonitrile butadiene styrene (ABS) resin mixture, such resin mixtures combining the highly transformable properties known to ABS copolymers, with the excellent mechanical properties, shock resistance and heat resistance properties known to polycarbonates.

According to yet another object, the tubular body extends along at least a part of a length of the elongated body of the handheld injection syringe. Preferably and advantageously however, the tubular body extends in parallel when mounted to the syringe body, for example via the cradle, along the entire length of the syringe body, such that the support body and the syringe body have the same, or substantially the same, lengths. When the syringe body is mounted onto the support body of the dose capture device, the longitudinal axis of the syringe body and the longitudinal axis of the bore of the support body, are aligned in parallel, and yet spaced apart from one another.

According to a further object, the support body comprises a mount, adapted and configured to receive at least a part of the displacement replicator system. The mount is dimensioned and shaped to house at least part of the displacement replicator system, as will be described in more detail hereafter. The mount is also configured to allow movement of at least a part of the displacement replicator within and through the mount along the central longitudinal axis of the support body. As the mount is advantageously located within the bore of the support body.

To this end, and according to yet another object, the mount is a fixed nut, having an internally threaded bore. The nut is fixed within the bore of the tubular support body, for example, by press fitting, gluing, adhering, or ultrasound welding, or any other appropriate fixation means that prevents the nut from moving within the bore, either by rotation, or by translating along the length of the bore of the tubular support body. As such, the nut is incapable of movement. The nut comprises a bore having an inward, i.e. into the bore, facing surface that is provided with a thread configured for engagement with the displacement replicator system.

The nut is advantageously made of a material having a low, or relatively low, coefficient of friction, in order to reduce friction with the displacement replicator system as much as possible, and as will be described in more detail hereafter. Generally, the nut is made of a plastic or polymeric material with a relatively high degree of hardness combined with a low coefficient of friction. The choice of an appropriate degree of hardness and coefficient of friction for the nut are considered to fall within the general knowledge of the skilled person. As a non-limitative, illustrative example, however, of suitable materials for the nut, one can cite those made commercially available under the name Iglidur® through the company IGUS (France), for example, from their range of sleeve bearings identified under the reference J350.

As mentioned above, the dose capture device also comprises a displacement replicator system, adapted and configured to replicate a translational movement of the plunger, in parallel to the longitudinal axis of the syringe body. Such a system is designed to replicate any translational displacement effected by the plunger of the syringe, whether in a proximal, or a distal direction.

Accordingly, in a further object, the displacement replicator system comprises a shaft having an external threading located on an outer surface of the shaft. The external threading of the shaft is configured and dimensioned to engage, and cooperate with the internal threading of the nut provided in the support body. The shaft can be made of any suitable material, for example, metal or a suitably resistant plastics material, but advantageously, the shaft is made of metal, and preferably stainless steel. An illustrative non-limitative example of a suitable threaded shaft is commercially available through the company IGUS (France), for example, under the dryspin® lead screw product reference. It will be understood from the above that the displacement replicator system is also configured to rotate about the longitudinal axis of the support body, simultaneously with the translational movement along said axis of the support body.

As a result of the above, and according to yet a further object, the shaft of the displacement replicator system is at least partially housed within the central bore of the tubular body of the support body. When the dose capture device is being used with unfilled syringes, for example, the displacement replicator system is so configured that when the dose capture device is first mounted onto the syringe body, or vice-versa, the shaft is substantially, or almost completely housed within the bore of the tubular support body. The proximal extremity of the shaft of the displacement replicator system, however, extends beyond the proximal extremity of the tubular support body. Alternatively, when the dose capture device is being used with pre-filled syringes, for example, the shaft will initially only be partially housed within the central bore of the tubular body of the support body, and in particular, only a distal part of the shaft including the distal extremity will be housed in the tubular body of the support body.

According to another object of the invention, the displacement replicator system further comprises a magnetic field producing means. Various means for producing a magnetic field are known, for example, classical magnets, electromagnets, and mixed material magnets. Such magnets are typically made from magnetizable materials, having magnetic or paramagnetic properties, whether naturally or when an electric or other energizing flow traverses or affects said material to produce or induce a magnetic field in said material. Suitable materials can be appropriately selected from:

ferrite magnets, especially sintered ferrite magnets, for example, comprising a crystalline compound of iron, oxygen and strontium;

composite materials consisting of a thermoplastic matrix and isotropic neodymium-iron-boron powder;

composite materials made up of a thermoplastic matrix and strontium-based hard ferrite powder, whereby the resulting magnets can contain isotropic, i.e. non-oriented, or anisotropic, i.e. oriented ferrite particles;

composite materials made of a thermo-hardening plastic matrix and isotropic neodymium-iron-boron powder;

magnetic elastomers produced with, for example, heavily charged strontium ferrite powders mixed with synthetic rubber or PVC, and subsequently either extruded into the desired shape or calendered into fine sheets;

flexible calendered composites, generally having the appearance of a brown sheet, and more or less flexible depending on its thickness and its composition. These composites are never elastic like rubber, and tend to have a Shore Hardness in the range of 60 to 65 Shore D ANSI. Such composites are generally formed from a synthetic elastomer charged with strontium ferrite grains. The resulting magnets can be anisotropic or isotropic, the sheet varieties generally having a magnetic particle alignment due to calendering;

laminated composites, generally comprising a flexible composite as above, co-laminated with a soft iron-pole plate;

neodymium-iron-boron magnets;

steels made of aluminium-nickel-cobalt alloy and magnetized;

alloys of samarium and cobalt.

Of the above list of magnetic field producing means suitable for use in the present invention, those selected from the group consisting of neodymium-iron-boron permanent magnets, magnetic elastomers, composite materials made up of a thermoplastic matrix and strontium-based hard ferrite powder, and composite materials made of a thermo-hardening plastic matrix and isotropic neodymium-iron-boron powder, are preferred. Such magnets are known for their ability to be dimensioned at relatively small sizes whilst maintaining relatively high magnetic field strength.

Whilst the magnetic field producing means can be of any suitable general shape, for example disk-shaped, including circular, ellipsoid, or any other suitable polygonal shape, a single magnet advantageously has only a single dipole. Although the magnetic field producing means can be substantially disk-shaped, such a disk-shape can also include magnets which have an orifice substantially in the centre of the disk to form a ring or annular shaped magnet.

According to another object of the invention therefore, the magnetic field producing means comprises at least one of an annular dipole magnet, a disk-shaped dipole magnet, or at least one pair of diametrically located N-S dipole magnets.

According to one advantageous object of the invention, the magnetic field producing means comprises two diametrically aligned single dipole magnets, in which the magnets are aligned across a diameter at opposite positions of said diameter. The term "alignment" or "aligned" as used herein, refers to the poles of the magnets being aligned along a longitudinal axis of each magnet. Such a configuration can be achieved, for example, through the use of small disk-shaped, rod-shaped or cylindrical magnets having a first and second ends, a first pole being located substantially at a first end and a second and opposite pole being located substantially at the second end of the magnet. Each magnet is then located at opposite positions on a circumference of the diameter such that the poles of the magnets are in alignment one with the other along said longitudinal axis of the magnet. The magnetic poles of each magnet can be respectively be positioned inverted one with respect to the other, for example in a N-S/S-N arrangement or a S-N/N-S arrangement, but preferably and advantageously, the magnetic poles are positioned in a repeat configuration in which the poles are aligned in a N-S/N-S or a S-N/S-N arrangement along the longitudinal axis of the magnets.

According to yet a still further object, the magnetic field producing means is mounted fixed in co-rotation with the shaft. In other words the magnetic field producing means rotates in the same rotational direction and to the same degree of rotation, as the shaft, when the shaft is rotated. Advantageously, the magnetic field producing means is mounted at, or adjacent, the proximal extremity of the shaft, and in particular adjacent the proximal extremity of the shaft that projects in a proximal direction beyond the proximal extremity of the tubular support body. The length of the shaft is dimensioned to correspond, and remain functionally effective, with regard, to the maximum possible axial distance of travel of the plunger head of the injection syringe, however, shorter lengths of shaft can also be foreseen, for the eventuality that the dose capture device is only intended to measure a more limited degree of translational axial travel of the plunger head in a proximal or distal direction.

As mentioned above, the magnetic field producing means is mounted to the shaft. In order to avoid and/or limit the potential for magnetisation of a part, or all of the shaft, for example, when the shaft is made of metal, and according to yet another object of the invention, the magnetic field producing means can advantageously further comprise a magnet holder body, for example, made of suitable plastics or polymeric material, such as a polycarbonate (PC)/acrylonitrile butadiene styrene (ABS) resin mixture, as described herein, and the magnet holder body provided with at least a receiving portion configured to receive and orient the magnet or magnets into the correct spatial orientation about the shaft. Alternatively, if the shaft is made of non-metallic material, then the magnet or magnets could be mounted directly to the shaft, or alternatively, also located within a magnet holder body. Preferably, and advantageously, the magnet holder body is a sleeve, with a bore that is dimensioned to allow insertion of the shaft therethrough, for example, press fit insertion or, attachment of the magnet holder body through gluing, adhering, or any appropriate fixation means, for example welding, such as ultrasound welding, depending on the materials used for the magnet holder body and the shaft, respectively. In particular, and in one envisaged configuration, the magnet holder body comprises two diametrically opposed recesses, which are dimensioned to each receive a single dipole magnet, the magnet being positioned in the recess such that the poles are aligned through a polar axis of the magnets across the diameter of the magnet holder body and shaft, for example N-S/N-S, or S-N/S-N. Alternatively, a first dipole magnet is positioned in a first recess of the magnet holder body in a first polar orientation, and a second dipole magnet is positioned in a second recess diametrically opposed to the first recess, in a second polar orientation, the second polar orientation being the inverse of the first polar orientation, for example N-S/S-N, or S-N/N-S.

It will be understood from the above that as the shaft is moved in either a proximal or distal direction, via cooperation of the threaded surface of the shaft with the threaded surface of the nut, and correspondingly out of, or into the tubular support body, the shaft will be caused to rotate about the longitudinal axis of the tubular body. During rotation of the shaft, the magnetic field producing means, including magnet, or magnets, and magnet holder body where present, are also caused to rotate to the same degree as the shaft, due to the fixed rotational relationship between the magnetic field producing means and the shaft. In this way, one or more magnetic fields are produced about the longitudinal axis of the tubular body, in parallel to the longitudinal axis of the elongated body of the injection syringe.

According to yet another object, the at least one sensor is a magnetometer. Such a magnetometer differs from the GMR, AMR or TMR sensors in that it directly measures magnetic field strength. Magnetometers measure magnetic fields in two main ways: vector magnetometers measure the vector components of a magnetic field, and total field magnetometers or scalar magnetometers measure the magnitude of the vector magnetic field. Another type of magnetometer is the absolute magnetometer, which measures the absolute magnitude or vector magnetic field, using an internal calibration or known physical constants of the magnetic sensor. Relative magnetometers measure magnitude or vector magnetic field relative to a fixed but uncalibrated baseline, and are also called variometers, used to measure variations in magnetic field. A preferred magnetometer therefore for use in dose capture device according to the present invention is an ultra low-power high performance three axis Hall-effect magnetometer. The magnetometer is accordingly configured to measure magnetic field over two or three mutually perpendicular or orthogonal axes.

According to another object of the invention, the sensor, for example, the magnetometer, is located along the central longitudinal axis of the support body. In this way, the sensor is centrally aligned with respect to the rotating magnetic fields provided by the magnetic field producing means, which form a multidimensional, preferably at least a 2-dimensional, and even more preferably a 3-dimensional magnetic field around said central longitudinal axis of the tubular support body.

According to yet another object, the at least one sensor is an accelerometer. Such sensors are known per se in the art, and include single and multiple-axis accelerometers. Whilst there exist many different types of accelerometer on the market, a suitable accelerometer as envisaged herein is a low-g three-axis accelerometer. The accelerometer is responsible for detecting and/or measuring changes in relative movement due to acceleration, of the drug delivery device, on which the dose capture device is mounted, be it from a horizontal to vertical position as held by the user, or any position in between, with regard to a set of pre-determined and pre-programmed reference positions. The strength and frequency of the relative movements of acceleration, which are communicated from the accelerometer to the processing system, are used to determine the type of operation that the user has effected. In particular, the accelerometer is configured to detect a positional orientation of the syringe having the dose capture device mounted thereon, chosen from at least one or more of an injection priming position, a syringe purge position, and an injection ejecting position. An injection priming position is a position in which the syringe is primed for injection, which is generally a substantially horizontal position, in which the dose of injectable substance to inject has been selected by the user. An injection purge position is a position in which the syringe body is ready to be, or has been, purged of any residual air, which is generally a substantially vertical position with the needle, or distal extremity of the syringe body, pointing upwards, although allowances are often made for a maximum angle from the vertical still being considered by the processing system as the purge position, for example a maximum angle from the vertical of approximately 30° to 45°. An injection ejecting position is a position in which the syringe body is pointing in a substantially downwards orientation, with the distal extremity of the syringe, and/or needle, facing downwards towards the site of injection and/or ejection of the injectable substance, enabling injection of the injectable substance into or onto the subject.

As has been mentioned above, the dose capture device comprises at least one sensor, for example a magnetometer and accelerometer, but also a processing system. According to yet another object, the processing system and at least one sensor are in communication one with the other, and the processing system is configured to process signals received from the at least one sensor. In the case of a magnetic sensor as described herein, the magnetic sensor detects magnetic fields produced by the magnetic field producing means and relays changes in measured magnetic field to the processing system as the magnetic field producing means rotates around, and is moved along, either proximally or distally, the central longitudinal axis of the tubular support body. The processing system comprises an integrated control and data processing unit, such as at least one micro-controller, connected electrically to the magnetic field sensor for processing information received from the magnetic field sensor. The processing system and at least one sensor can be integrated into an electronic component board such as, for example, a printed circuit board of correspondingly appropriate dimensions that will vary according to the desired location of the electronic component board within the dose capture device. The integrated control and data processing unit, comprising at least one micro-controller, handles all electrical communication and signalling between the different electronic components of the processing system and the magnetic field sensor. The at least one microcontroller is in electrical communication with at least one of a memory, an autonomous power supply, and a communications unit.

The processing system is also responsible for execution of the calculations which enable the precise positional location of the magnetic field producing means to be calculated and determined, as well as handling signals from the autonomous power supply and the communication means, the latter being configured to optionally communicate with another local or remote data processing system, e.g. on a smartphone. The processing system, via the at least one microcontroller, can be programmed remotely, upon first use, or receive information and updates, in a similar way to other electronic devices today containing integrated control and data processing units. Such integrated control and data processing units are known per se, and often integrate a central processing unit, a real time clock, one or more memory storage systems, and optionally communications systems or subsystems, along with other desired components.

The processing system is powered electrically by an autonomous power supply, for example, a removable and/or rechargeable power supply. Such a removable, autonomous, power supply can usefully be, for example, a lithium ion battery, which can be easily exchanged when depleted, or alternatively, a rechargeable battery, which can be charged up when depleted for example via a corresponding charging port, such as a USB charging port, provided in the dose capture device, and connected to the rechargeable battery, both types of battery being generally known to the skilled person.

The communications unit can be, for example, any suitable radiofrequency transmissions unit, such as a Bluetooth communications unit, and advantageously a Bluetooth Low Energy circuit (BLE), enabling data to be sent from, and received by, the processing system to, and respectively from, a remote terminal device, such as a suitably equipped smartphone, remote computing system, or distributed computing system.

The at least one sensor and processing system as described above are located within the dose capture device. Advantageously, where the sensor is a magnetic field sensor, and the magnetic field producing means are located around the shaft of the displacement replicator system, then the at least one sensor and processing system are located somewhere along, and advantageously, at either end of, the longitudinal axis of the tubular support body, in order to obtain the most accurate results from the processing system. Accordingly, the at least one sensor and processing system can, in one advantageous configuration, be housed within the coupling means. According to an alternative object, the at least one sensor and processing means can be housed within the support body.

The coupling means will be described in more detail hereafter. The coupling means serves to couple the injection syringe plunger to the displacement replicator system. Ideally therefore, the coupling means comprises a first receiving portion, configured and adapted to receive at least a portion of a plunger head located at the proximal extremity of the plunger. The receiving portion of the coupling means is dimensioned to allow at least a part of the plunger head to be inserted and received therein, yet at the same time surround said at least part of the plunger head, such that when the coupling means is pushed in a distal direction, or pulled in a proximal direction, the coupling means moves the at least part of the plunger head directly. To that extent, the receiving portion of the coupling means comprises engagement surfaces that snugly surround and engage with said at least part of the plunger head to transmit any proximal or distal movement of the coupling means to the plunger head.

According to yet a further object, the coupling means also comprises a second receiving portion, configured and adapted to receive at least a portion of a proximal extremity of the displacement means. Similarly, to the first receiving portion, the second receiving portion is dimensioned to receive and engage with the proximal extremity of the shaft, such that any proximal or distal movement of the plunger head is transmitted via the coupling means to the proximal extremity of the shaft of the displacement replicator system. In this manner, the proximal extremity of the displacement replicator system is moved in a proximal or distal direction according to the corresponding direction of movement of the plunger. As has been mentioned elsewhere in the present application, distal or proximal movement of the shaft causes the magnetic field producing means to rotate about the central longitudinal axis of the tubular support body to the same degree as the rotation of the displacement replicator shaft.

Additionally, in an alternative embodiment in which the magnetic field sensor is for example located on or within the support body, and along or on the longitudinal axis of the support body, any movement of the magnets towards the magnetic field sensor will show an increase in the strength of measured magnetic field, and movement away from the magnetic field sensor will show a decrease in the strength of measure magnetic field.

Advantageously, and in a preferred embodiment, the sensor is configured to report magnetic field measurements for any given angle of rotation, which means that even if the magnetic field producing means and the magnetic sensor maintain a fixed length distance one from the other, for example, when the sensor is located within the coupling means, then the number of rotations of the magnet about the axis of the tubular support body are still detected.

All of the above relative measurements are thus processed by the processing system, and used to correlate a distance travelled by the displacement replicator system to a distance travelled by the plunger, respectively the plunger head. That correlated distance travelled by the plunger is then converted by the processing system into a dose selected, and/or ejected, by the user.

According to yet another object, the second receiving portion of the coupling means is further configured to receive a magnetic field producing means of the displacement replicator system. This feature allows the magnetic field producing means to be received within the second receiving portion. The second receiving portion not only therefore is dimensioned to receive and engage with the proximal extremity of the displacement replicator shaft, but also, and according to yet another object, provide sufficient space for the magnetic field producing means to permit free-rotation of the magnetic field producing means about the longitudinal axis of the support body, within said second receiving portion. The expression "free rotation" should be understood here to mean that the receiving portion is sized, shaped and dimensioned to allow rotation of the magnetic field producing means as freely as possible within said second receiving portion with a minimum of friction. An appropriate selection of the materials used for both the magnetic field producing means and the receiving portion of the coupling means will lead to desired result. For example, as has been mentioned elsewhere in the present application, where the magnetic field producing means comprises a magnet holder body, and that body is made of PC/ABS, then the second receiving portion of the coupling means can also be made of PC/ABS.

Accordingly, as will be understood from the above, a further object is that the coupling means is configured to:

couple translational movement of the plunger of the handheld injection syringe in a proximal or distal direction to the displacement replicator means, and permit free rotation of the displacement replicator means in parallel alignment to the central longitudinal axis of the elongated body.

The coupling means can generally be represented as a proximal body of material, for example suitably moulded PC/ABS material, provided with corresponding first and second receiving portions. For example, the first receiving portion of the coupling means can be provided through a suitably sized and oriented slot in the body that receives the plunger head, said slot comprising at least one engagement surface that cooperates and engages with a corresponding engagement surface of the plunger head. Similarly, the proximal body of the coupling means can be provided with a recess defining the second receiving portion, said recess being spaced apart from, yet aligned in parallel with the axis of the injection syringe, such that when the proximal extremity of the displacement replicator means is introduced into said second receiving portion, the axis of the injection syringe body and the axis of the tubular support body are in parallel, spaced apart alignment. The coupling means body can be provided with suitable optional separating walls and projections that might be desired to contain each of the plunger head and the magnetic field producing means within their first, and second, receiving portions respectively.

Furthermore, and as mentioned elsewhere in the present application, the at least one sensor and processing system are housed within the coupling means. To that end, the coupling means comprises a third receiving portion, configured and dimensioned to receive said at least one sensor and processing system. The third receiving portion is typically formed as part of the body of the coupling means, for example as a well, defined by corresponding side walls extending in a proximal direction from a base, the well receiving the at least one sensor and processor system, wherein the at least one sensor is positioned in axial alignment with the central longitudinal axis of the tubular support body. Generally, the third receiving portion is positioned axially and proximally of the second receiving portion, such that the magnetic field production means rotates with the displacement locator shaft about the magnetic field sensor which is correspondingly located proximally and axially on the axis of rotation. In this way, even if the magnetic field production means maintains a constant axial distance with the magnetic sensor, changes in axial proximal or distal movement of the plunger head can still be registered as revolutions of the magnetic field producing means about the magnetic sensor.

In yet a further object of the invention, a method is provided for capturing a dose selected, or ejected, by a user of a handheld injection syringe comprising an elongated body having a longitudinal bore defining a central longitudinal axis, the elongated body having a proximal extremity and a distal extremity, and a syringe plunger located within, and movable along said central longitudinal axis of said bore, the syringe plunger extending beyond said proximal extremity, the method comprising:

attaching a handheld dose capture device as described herein, to the handheld injection syringe, the coupling means of said dose capture device receiving at least a portion of a plunger head located at the proximal extremity of the plunger in a first receiving portion of said coupling means;

moving the plunger head of the handheld injection syringe in a distal, and/or a proximal, direction;

replicating the movement of the plunger head via the displacement replicator system;

detecting the replicated movement the displacement replicator system via at least one sensor located in the coupling means and/or the support body;

correlating said detected replicated displacement movement via processing means connected to the at least one sensor, to provide a captured dose corresponding to a dose set, and/or a dose expelled, by the user;

storing said captured dose within the processing means for one of dose logging, communication to a remote receiver, or display of the captured dose.

According to yet a further object of the invention, the method is further defined wherein:

the detection of the replicated movement comprises sensing a change in a magnetic field produced by rotation of a magnetic field producing means provided by the displacement replicator system, and correlating said changes in magnetic field to a distance moved by the plunger; and calculating from said correlated distance moved a dose set, and/or ejected, by the user of the handheld injection syringe.

The invention will now be described in further detail in relation to the figures, provided for illustrative purposes of one or more embodiments, in which.

EXAMPLE

Figure 1:
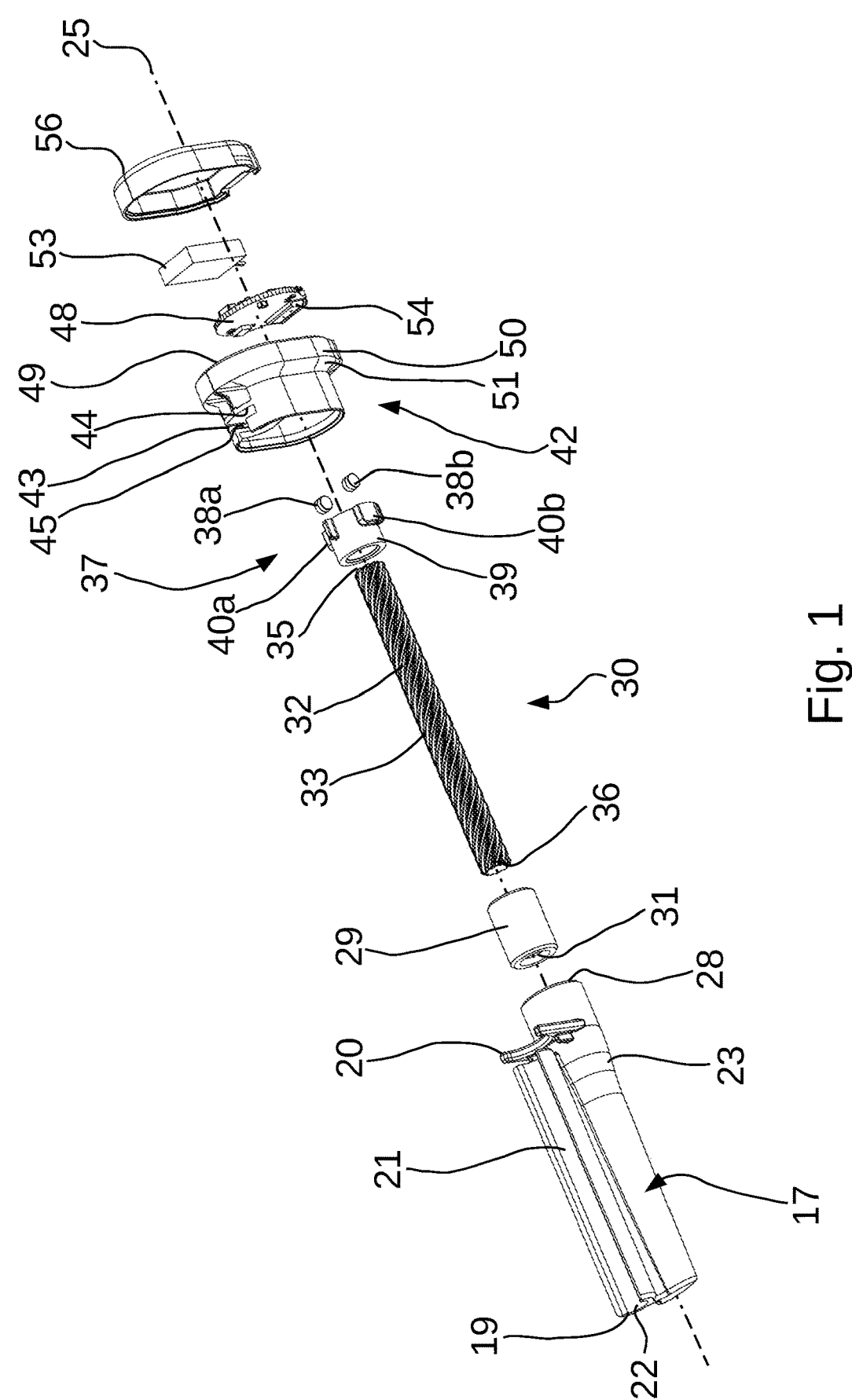
FIG. 1 is a schematic perspective exploded view of a handheld dose capture device for a handheld injection syringe.
Figure 2:
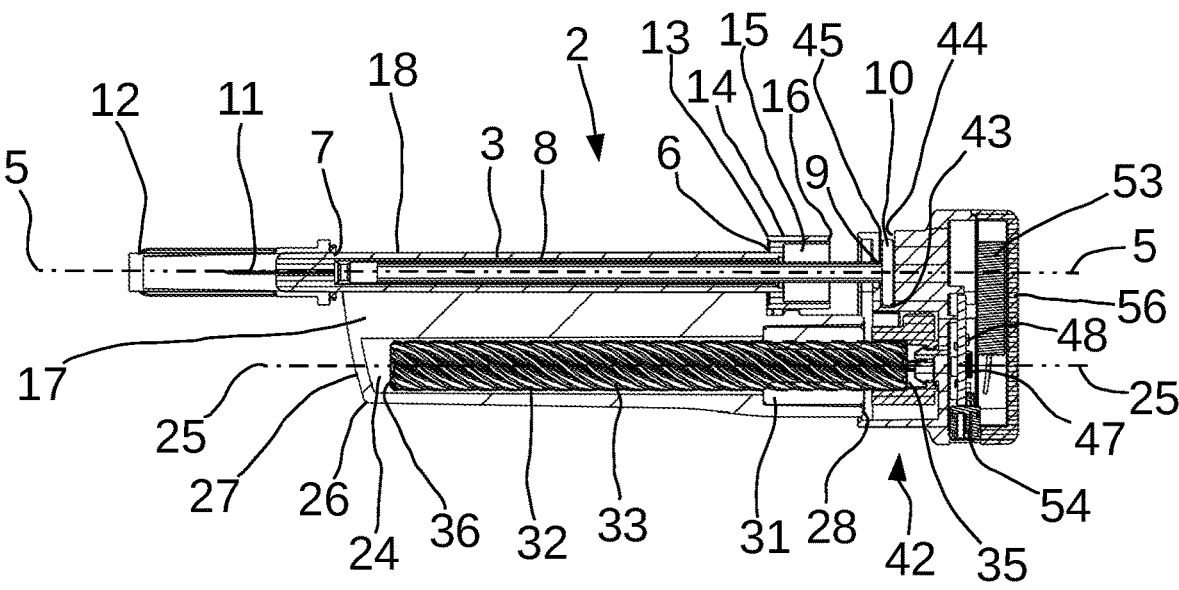
FIG. 2 is a schematic cross-sectional view of the handheld dose capture device of FIG. 1 mounted to an injection syringe with needle.

Turning to FIGS. 1 and 2, a schematic perspective exploded view (FIG. 1), and a cross-sectional view (FIG. 2), of a handheld dose capture device (1) according to the invention, and adapted to be releasably attached to a handheld injection syringe (2), such as a hypodermic syringe. The hypodermic syringe (2) is of the type known commonly available in commerce, and comprises an elongated syringe body (3) having a longitudinal bore (4) defining a central longitudinal axis (5), the elongated body (3) having a proximal extremity (6) and a distal extremity (7), and a syringe plunger (8) located within, and movable along said central longitudinal axis (5) of said bore (4), the syringe plunger (8) extending beyond the proximal extremity (6) of the elongated body (3). The plunger (8) is terminated at a proximal extremity (9) thereof by a plunger head (10), and the syringe body (3) is closed at the distal extremity thereof (7) by a hypodermic injection needle (11) or cannula, covered by a protective cap (12). At the proximal extremity (6) of the syringe body (3), the body is provided with an annular skirt (13) which projects radially outwardly, with an annular wall (14) extending in the proximal direction from the periphery of the annular skirt (13), and which together define a well (15). The well (15) defined by the skirt (13) and annular wall (14) can be dimensioned to be able to completely receive the plunger head (10) within the well (15), or alternatively, a proximal extremity (16) of the annular wall can serve as a stopping abutment for any distal direction movement of the plunger head.

The dose capture device (1) comprises a support body (17), which is configured to releasably connect, clip onto, or otherwise engage with at least an outer surface (18) of the elongated body (3) of the handheld injection syringe (2) in parallel alignment to the central longitudinal axis (5) of said elongated body (3). The support body (17) therefore comprises a cradle (19) for releasably contacting at least an outer surface of the elongated body of the handheld injection syringe, which extends along substantially at least a part of the length of the syringe body (3), as illustrated in FIG. 2, thereby allowing for locating of finger lugs formed by the radially outwardly projecting annular skirt (13). In addition, the support body (17) is provided with a correspondingly sized cradle fork (20), having an appropriately dimensioned radius of curvature to accept the radius of curvature of an outer surface of the proximally projecting extremity formed by the annular skirt (13) and annular wall (14) of the syringe body (3). The cradle (19) is configured with an outwardly projecting concave curved wall (21), extending from the support body (17), for example, that either substantially matches the radius or curvature of the outer surface (18) of the syringe body (3), or alternatively is of slightly narrower radius of curvature than the outer surface (18) of the syringe body (3). The cradle wall (21) forms a longitudinally oriented hollow or groove (22), shaped to receive and retain the body (3) of the syringe (2) for the duration of use of the syringe. The cradle wall (21) of the support body (17) is advantageously made of elastically deformable material, such that when the syringe body is pushed against the cradle, it snap-fits, or push-fits into the longitudinally formed groove (22) via elastic deformation of the cradle wall (21). Once the syringe body is seated within the longitudinal groove (22), the elastic recall of the cradle wall (21) material forces the cradle wall (21) to engage with and securely hold the outer surface (18) of the syringe body (3). Similarly, when the syringe is spent, the syringe body can be removed from the cradle by elastically deforming the walls (21) of the cradle (19) once again to ease, or pull force, out the syringe body (3) and free it from the support body (17).

The support body further comprises a tubular body (23), having a longitudinal central bore (24) defining a longitudinal axis (25) that is located parallel to the longitudinal axis (5) of the elongated body (3) of the injection syringe (2) when the dose capture device (1) is mounted on the handheld injection syringe (2). The tubular body (23) and cradle wall (21) are attached one to the other by any appropriate means, and are made, for example, of one and the same material, for example, a suitable plastic or polymeric material, for example, obtained by injection and/or blow moulding. Suitable polymeric materials for the cradle (21) and tubular body (23) are polycarbonate (PC)/acrylonitrile butadiene styrene (ABS) resin mixtures, such resin mixtures combining the highly transformable properties known to ABS copolymers, with the excellent mechanical properties, shock resistance and heat resistance properties known to polycarbonates.

The tubular body (23) extends along at least a part of a length of the elongated body (3) of the handheld injection syringe (2). As illustrated in FIG. 2, the tubular body extends in parallel, when mounted to the syringe body (3), along the entire length of the syringe body (3), such that the support body (17) and the syringe body (3) have the same, or substantially the same, lengths. When the syringe body (3) is mounted onto the support body (17) of the dose capture device, the longitudinal axis (5) of the syringe body and the longitudinal axis (25) of the bore of the support body (17), are thus aligned in parallel, and yet spaced apart from one another. The bore (24) of the tubular body (23) is preferably, but not obligatorily, closed at a distal extremity (26) thereof by a wall (27) of material of the tubular support body (17).

A proximal extremity (28) of the bore (24) of the tubular body (23) is open, and contains a mount (29), dimensioned and configured to receive at least a part of the displacement replicator system (30). In the present example, the mount (29) is an internally threaded nut, which is seated in a fixed location within the bore (24) at the proximal extremity (28) of the bore (24). The mount (29) is also configured to allow movement of at least a part of the displacement replicator system (30) within and through the mount (29) along the central longitudinal axis (25) of the tubular body (23) of the support body (17). The mount (29), as exemplified in the Figures by an internally screw threaded nut, also comprises a bore (31) dimensioned to receive said part of the displacement replicator system (30). The nut (29) is fixed within the bore (24) of the tubular body (23) of the support body (17), for example, by press fitting, gluing, adhering, or ultrasound welding, or any other appropriate fixation means that prevents the nut from moving within the bore (24), either by rotation, or by translating along the length of the bore (24) of the tubular body (23). As such, the nut (29) is incapable of movement. The internal threading of the nut (29) is an inward, i.e. into the bore, facing surface that is configured for corresponding engagement with the displacement replicator system (30).

Figure 3:
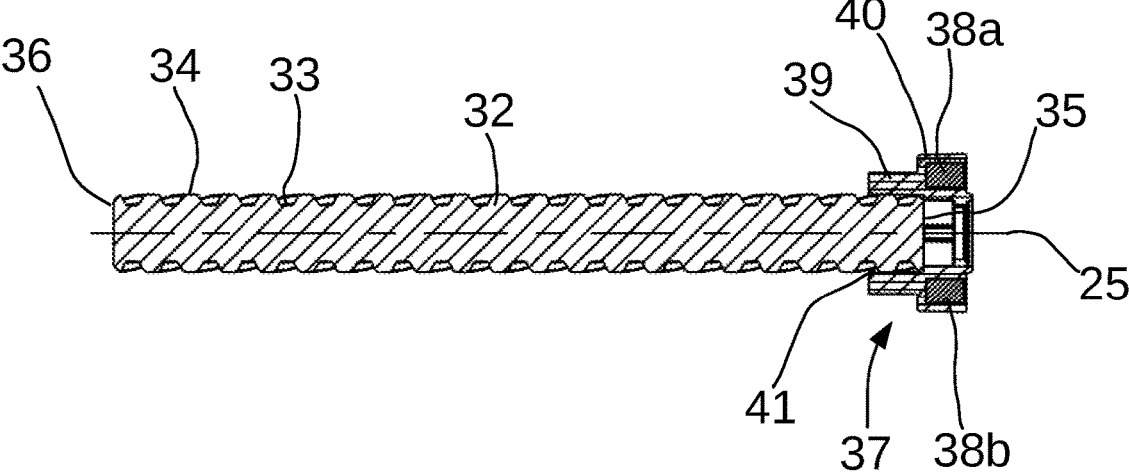
FIG. 3 is a schematic cross-sectional view of the displacement replicator system of the dose capture device of FIG. 1

The displacement replicator system (30) is adapted and configured to replicate a translational movement of the plunger, in parallel to the longitudinal axis (5) of the syringe body (3). Such a system (30) is designed to replicate any translational displacement effected by the plunger (8) of the syringe (3), whether in a proximal, or a distal direction. As illustrated in FIGS. 1, 2 and 3, the displacement replicator system comprises a shaft (32) having an external screw threading (33) located on an outer surface (34) of the shaft. The external screw threading (33) of the shaft (32) is configured and dimensioned to engage, and cooperate with the internal threading (31) of the nut mount (29) provided in the tubular body (23) of the support body (17). The shaft (32) can be made of any suitable material, for example, metal or a suitably resistant plastics material, but advantageously, the shaft is made of metal, and preferably stainless steel. The shaft (32) is at least partially housed within the central bore (24) of the tubular body (23) of the support body (17). The displacement replicator system (30) is so configured that when the dose capture device (1) is first mounted onto the syringe body (3), or vice-versa, the shaft (32) is substantially, or almost completely housed within the bore (24) of the tubular body (23) of the support body (17), as shown in FIG. 2. The proximal extremity (35) of the shaft (32) of the displacement replicator system (30) extends beyond the proximal extremity (28) of the tubular body (23), whereas the distal extremity (36) of the shaft (32) is housed within the bore (24) of the tubular body (23) of the support body (17) and prevented from extending beyond the distal extremity (26) of the tubular body (23) by the distal wall (27).

The displacement replicator system (30) further comprises a magnetic field producing means (37), and as illustrated in the figures, the magnetic field producing means (37) is mounted at, or adjacent, the proximal extremity of the shaft (32), and in particular adjacent the proximal extremity (35) of the shaft (32) which projects in a proximal direction beyond the proximal extremity (28) of the tubular body (23) of the support body (17). The length of the shaft (32) is dimensioned to correspond, and remain functionally effective, with regard, to the maximum possible axial distance of travel of the plunger head (10) of the injection syringe (3), however, shorter lengths of shaft (32) can also be foreseen, for the eventuality that the dose capture device (1) is only intended to measure a more limited degree of translational axial travel of the plunger head (10) in a proximal or distal direction.

Generally, the magnetic field producing means (37) will be provided by one or more magnets, electromagnets, and/or mixed material magnets as has been elsewhere herein. As illustrated in FIGS. 1, 2 and 3, the magnetic field producing means are represented by a pair (38a, 38b) of single dipole disk-shaped, or rod-shaped magnets. The magnets (38a, 38b) are mounted to the shaft (32) such that rotation of the shaft (32), as the shaft (32) is moved in a proximal or distal direction through interaction of the external screw thread (33) of the shaft (32) with the internal screw thread (31) of the nut mount (29), causes the magnets (38a, 38b) to rotate with the shaft (32) about the longitudinal axis (25). In order to avoid and/or limit the potential for magnetisation of a part, or all of the shaft, for example, when the shaft is made of metal, the magnetic field producing means (37) further comprise a magnet holder body (39), for example, made of a suitable moulded plastics or polymeric material, such as a polycarbonate (PC)/acrylonitrile butadiene styrene (ABS) resin mixture, as described elsewhere herein. The magnet holder body (39) is provided with at least a receiving portion (40) configured to receive and orient the magnet or magnets (38a, 38b) into the correct spatial orientation about the shaft. If the shaft is made of non-metallic material, then the magnet or magnets (38a, 38b) can be mounted directly to the shaft, or alternatively, also located within a magnet holder body (40). As illustrated in the figures, the magnet holder body (39) is a sleeve, with a bore (41) that is dimensioned to allow insertion of the shaft therethrough, for example, via press fit insertion or, attachment of the magnet holder body (39) through gluing, adhering, or any appropriate fixation means, for example welding, such as ultrasound welding, depending on the materials used for the magnet holder body (39) and the shaft (32), respectively. As illustrated in the Figures, the magnet holder body (39) is configured with a receiving portion (40) which comprises two diametrically opposed recesses (40a, 40b), each of which is dimensioned to receive a single dipole magnet (38a, 38b), the magnet (38a, 38b) being positioned in the recess such that the poles are aligned through a polar axis of the magnets (38a, 38b) across the diameter of the magnet holder body (39) and shaft (32), for example in a N-S/N-S polar aligned configuration, or a S-N/S-N polar aligned configuration. Alternatively, a first dipole magnet (38a) is positioned in a first recess (40a) of the magnet holder body in a first polar orientation, and a second dipole magnet (38b) is positioned in a second recess (40b) diametrically opposed to the first recess (40a), in a second polar orientation, the second polar orientation being the inverse of the first polar orientation, for example N-S/ S-N, or S-N/N-S.

It will be understood from the above that as the shaft (32) is moved in either a proximal or distal direction, via cooperation of the threaded surface (33) of the shaft (32) with the threaded surface (31) of the nut mount (29), and correspondingly out of, or into the tubular body (23), the shaft (32) will be caused to rotate about the longitudinal axis (25) of the tubular body (23). During rotation of the shaft, the magnetic field producing means (37), including magnet, or magnets (38a, 38b), and magnet holder body (39), are also caused to rotate to the same degree as the shaft (32), due to the fixed rotational relationship between the magnetic field producing means (37) and the shaft (32). In this way, one or more magnetic fields are produced about the longitudinal axis (25) of the tubular body (23), in parallel to the longitudinal axis (5) of the elongated body (3) of the injection syringe (2).

The dose capture device (1) further comprises a coupling means (42), which serves to couple the injection syringe plunger (8) to the displacement replicator system (30). The coupling means (42) comprises a first receiving portion (43), which is configured and adapted to receive at least a portion of the plunger head (10). The first receiving portion (43) of the coupling means (42) is dimensioned to allow at least a part of the plunger head to be inserted and received therein, yet at the same time surround said at least part of the plunger head, such that when the coupling means (42) is pushed in a distal direction, or pulled in a proximal direction, the coupling means (42) moves the at least part of the plunger head (10) directly, along the longitudinal axis (5) of the syringe body (3). The first receiving portion (43) of the coupling means (42) therefore comprises engagement surfaces (44, 45) that snugly surround and engage with said at least part of the plunger head (10) to transmit any proximal or distal movement of the coupling means to the plunger head. For example, as illustrated in FIGS. 1 and 2, the coupling means (42) is represented by a body (46), for example a moulded body of plastics or polymeric material such as a PC/ABS resin mixture, having a first receiving portion (43) represented by a T-shaped slot comprising proximal (44) and distal (45) walls. The proximal and distal walls (44, 45) define the engagement surfaces of the first receiving portion (43), and act on, or cooperate with, the plunger head (10) when a force is exerted by the user through the coupling means (42) in either a proximal or distal direction, for example, when the user pushes or pulls the coupling means in a distal, or respectively proximal, direction.

Figure 4:
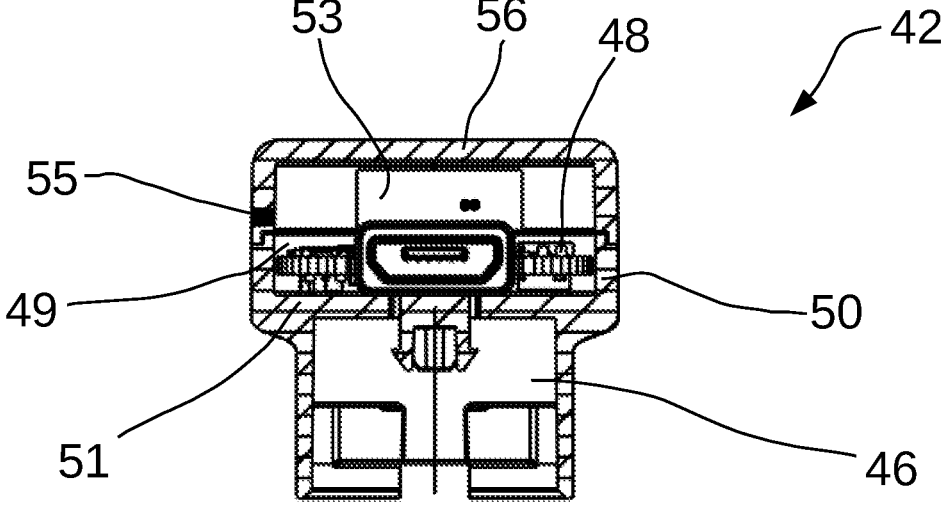
FIG. 4 is a schematic cross-sectional view of the coupling means of the handheld dose capture device of FIG. 1.

Additionally, the coupling means also comprise a second receiving portion (46), as illustrated in FIGS. 1, 2 and 4, configured and adapted to receive at least a portion of the proximal extremity (35) of the shaft (32) and magnetic field producing means (37). The second receiving portion (46) is dimensioned to receive and engage with the proximal extremity of the shaft (32), such that any proximal or distal movement of the plunger head (10) is transmitted via the coupling means (42) to the proximal extremity (35) of the shaft (32) of the displacement replicator system (30). In this manner, the proximal extremity (35) of the displacement replicator system (30) is also moved in a proximal or distal direction according to the corresponding direction of movement of the plunger (8). As has been mentioned elsewhere in the present application, distal or proximal movement of the shaft causes the magnetic field producing means (37) to rotate about the central longitudinal axis (25) of the tubular body (23) of the support body (17) to the same degree as the rotation of the displacement replicator shaft (32). The second receiving portion (46) of the coupling means (42) is further configured to receive the magnetic field producing means (37) of the displacement replicator system (30). The second receiving portion (46) is therefore not only dimensioned to receive and engage with the proximal extremity (35) of the displacement replicator shaft (32), but also provide sufficient space for the magnetic field producing means (37) to freely, or substantially freely, rotate about the longitudinal axis (25) of the tubular support (23) of the support body (17), within said second receiving portion (46). The expression "freely rotate", or "substantially freely rotate" should be understood here to mean that the second receiving portion (46) is sized, shaped and dimensioned to allow rotation of the magnetic field producing means (37) as freely as possible within said second receiving portion (46) with a minimum of friction. An appropriate selection of the materials used for both the magnetic field producing means (37) and the receiving portion (46) of the coupling means will lead to an acceptable result and functioning. For example, as has been mentioned elsewhere in the present application, where the magnetic field producing means (37) comprises a magnet holder body (39), and that body is made of PC/ABS, then the second receiving portion (46) of the coupling means can likewise also be made of PC/ABS.

As illustrated in the Figures, the dose capture device further comprises at least one sensor (47) and a processing system (48), and the at least one sensor (47) and processing system (49) are adapted and configured to correlate the translational movement of the displacement replicator system (30) with a selection and/or ejection of a dose of injectable substance operated by a user through the translational movement of the plunger (8) along the longitudinal axis (5). The processing system (48) and at least one sensor (47) are in communication one with the other, for example, via an electrical connection, and the processing system (48) is configured to process signals received from the at least one sensor (47). In the case of a magnetic sensor (47) as already described elsewhere in the present application, the magnetic sensor (47) detects magnetic fields produced by the magnetic field producing means (37) and relays changes in measured magnetic field to the processing system (48) as the magnetic field producing means (37) rotates around, and/or is moved along, either proximally or distally, the central longitudinal axis (25) of the tubular body (23). The processing system (48) comprises an integrated control and data processing unit, such as at least one micro-controller, connected electrically to the magnetic field sensor (47) for processing information received from the magnetic field sensor (47). The processing system (48) and at least one sensor (47) can be, as illustrated in the Figures, integrated into an electronic component board (52) such as, for example, a printed circuit board of correspondingly appropriate dimensions that will vary according to the desired location of the electronic component board (52) within the dose capture device. The integrated control and data processing unit, comprising at least one micro-controller, handles all electrical communication and signalling between the different electronic components of the processing system (48) and the magnetic field sensor (47).

The at least one sensor (47) is located along the longitudinal axis (25) of the tubular body (23) of the support body (17). In the example shown in FIGS. 1, 2, and 4, the sensor (47) and processing means (48) are housed within the coupling means (42), in a third receiving portion (49) provided therein. The third receiving portion (49) is configured and dimensioned to receive said at least one sensor (47)

and processing system (48). The third receiving portion (49) is typically formed as part of the body of the coupling means (42), for example as a well (49), defined for example, by a corresponding annular side wall (50), extending in a proximal direction from a base (51), the well (49) receiving the at least one sensor (47) and processor system (48), wherein the at least one sensor (48) is positioned in axial alignment with the central longitudinal axis of the tubular support body. Generally, the third receiving portion is positioned axially and proximally of the second receiving portion, such that the magnetic field production means rotates with the displacement locator shaft about the magnetic field sensor which is correspondingly located proximally and axially on the axis of rotation. In this way, even if the magnetic field production means maintains a constant axial distance with the magnetic sensor, changes in axial proximal or distal movement of the plunger head can still be registered as revolutions of the magnetic field producing means about the magnetic sensor.

The processing system further comprises at least one of a memory, an autonomous power supply (53), and a communications unit, whereby the at least one microcontroller is in electrical communication with these components, in order to receive power, on the one hand from the autonomous power supply (53), and be able to communicate data from and to the processing system with a remote receiver, such as a smartphone, or other telecommunications network, for example, the telephone network. The processing system (48) is furthermore responsible for execution of the calculations which enable the precise positional location of the magnetic field producing means (37) to be calculated and determined, as well as handling signals from the autonomous power supply (53) and the communication means. The processing system (48), via the at least one microcontroller, can be programmed remotely, upon first use, or receive information and updates, in a similar way to other electronic devices today containing integrated control and data processing units. Such integrated control and data processing units are known per se, and often integrate a central processing unit, a real time clock, one or more memory storage systems, and optionally also communications systems or subsystems, along with other desired components.

As mentioned above the processing system (48) is powered electrically by an autonomous power supply (53), for example, a removable and/or rechargeable power supply. Such a removable, autonomous, power supply can usefully be, for example, a lithium ion battery, which can be easily exchanged when depleted, or alternatively, a rechargeable battery, which can be charged up when depleted for example via a corresponding charging port, such as a USB charging port (54), provided in the dose capture device (1), and connected to the rechargeable battery, both types of battery being generally known to the skilled person. The autonomous power supply (53) can be appropriately housed in, or adjacent, the well of the third receiving portion (49), for example, located proximally and above the electronic component board, as illustrated in FIGS. 1, 2 and 4.

The communications unit can be, for example, any suitable radiofrequency transmissions unit, such as a Bluetooth communications unit, and advantageously a Bluetooth Low Energy circuit (BLE), enabling data to be sent from, and received by, the processing system to, and respectively from, a remote terminal device, such as a suitably equipped smartphone, remote computing system, or distributed computing system, via for example, a telecommunications network, or any other suitable communications network infrastructure.

The processing system can further comprise one or visible or audio producing signalling means, controlled by the microcontroller, and having outputs that can be either heard and/or seen outside of the dose capture device. For example, when the sensor and processing system are housed in the coupling means (42), said visible or audio producing signalling means can be provided with outlets in the body of the coupling means (42). As illustrated in FIG. 4, such a visible signal outlet means is provided by a light guide (55), for example for transmitting light from a light emitting diode included in the processing system to outside of the dose capture device (1). The light guide (54) can be conveniently located in either a peripheral wall (50) of the well (49), or alternatively, in a wall of a well cap (56), that covers the proximal opening of the well (49), and is dimensioned and configured to close the proximal well opening and enclose the autonomous power supply (53), processing system (48) and magnetic sensor (47).

The sensor (47), which is aligned with the longitudinal axis (25) of the tubular body (23), will report magnetic field measurements for any given angle of rotation of the magnetic field producing means (37), which means that even if the magnetic field producing means (37) and the magnetic sensor (47) maintain a fixed length distance one from the other, as illustrated in the Figures, then the number of rotations of the magnet about the axis of the tubular support body can still be detected. All of these measurements are processed by the processing system (48), and used to correlate a distance travelled by the displacement replicator system to a distance travelled by the plunger, respectively the plunger head. As the thread pitch of the shaft (32) is known in advance and included in the memory of the processing system (48) and included via corresponding programming executed by the processing system (48), and the translational distance travelled by the displacement replicator system (30) correlates directly to a distance of travel of the plunger head (10), in either a proximal or distal direction, that correlated distance travelled by the plunger head (10) is then converted by the processing system into a dose selected, and/or ejected, by the user, each time the plunger head (10) is moved, either distally or proximally. Similarly, in the case where the syringe does not already contain an injectable substance, moving the plunger head (10) in a proximal direction to withdraw an injectable substance from a substance container, for example, a vial, will cause the displacement replicator system to replicate said proximal movement, causing the magnets to rotate about the longitudinal axis (25), and the changes in magnetic field detected by the magnetic sensor contained in the coupling means (42) will be used by the processing system (48) to calculate a dose of substance withdrawn from the vial into the syringe. When the plunger is activated in an opposite direction, i.e. in a distal direction, to expel the injectable substance, the changes in magnetic field will be detected in a similar manner and used to calculate an expelled, or ejected dose of injectable substance by the processing system (48). The calculated set, withdrawn, or ejected dose can then be communicated outside of the device via the communications unit to, for example, via the Bluetooth communications protocol, to a suitably equipped smartphone or mobile device, for example, or a remote server, executing program code for handling, and/or displaying said captured dose to the user.

Figures 5A, 5B, 5C, 5D, 5E:
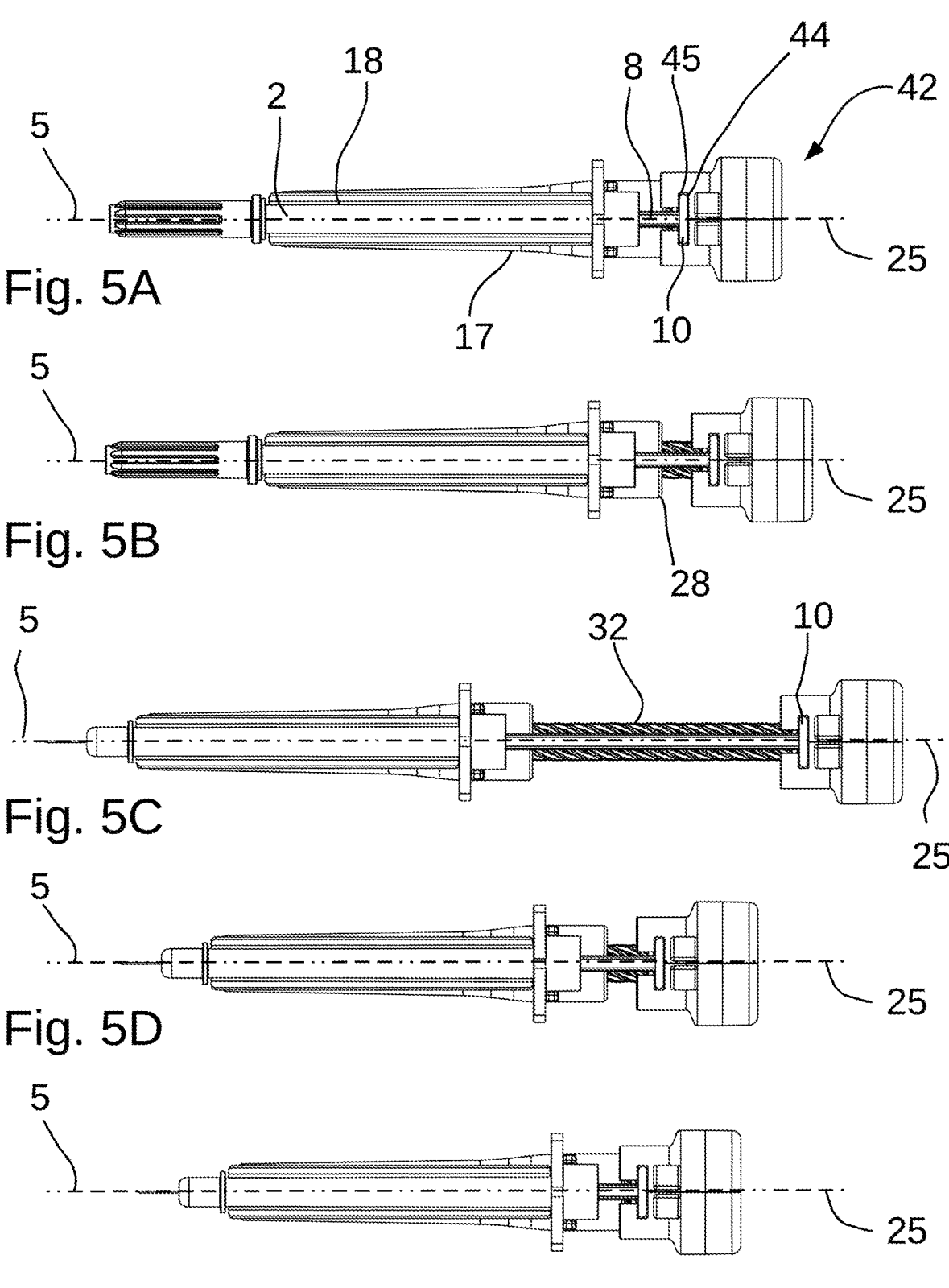
FIGS. 5A to 5E are schematic cross-sectional views illustrating the relative positions of the various components of the handheld dose capture device of FIG. 1 at different stages of use when mounted to the injection syringe.

In light of the above, a brief description of the functioning of the device, as illustrated FIGS. 5A to 5E, will be given herebelow. FIG. 5A schematically shows a representation of the dose capture device (1) according to the invention mounted to a 30 ml volume hypodermic syringe (2) via the cradle (18), and ready for use. In such an example, the syringe (2) already contains an injectable substance, such as a drug, for example, an injectable insulin product for the treatment of diabetes. In this view, the plunger head (10) is held by the engagement surfaces (44,45) of the first receiving portion (43) of the coupling means (42). In FIG. 5B, a user of the syringe has started to withdraw the plunger, by pulling, or moving the plunger head, for example by pulling on the coupling means (42) in a proximal direction. One can see from FIG. 5B that the displacement replicator system (30), and in particular, the shaft (32), is now visible beneath the syringe plunger (8). One can also see that the shaft (32) of the displacement system (30) is aligned in parallel with the longitudinal axis (5) of the syringe. The user continues to move the plunger head (10) in a proximal direction, i.e. generally towards the hand manipulating the coupling means (42), until a position is reached at which the user is satisfied that an appropriate dose of injectable substance has been selected, for example, as illustrated in FIG. 5C, to the maximum proximal extent of travel of the plunger head (10). In the meantime, the shaft (32) has been caused to rotate about the longitudinal axis (25) and consequently causes the magnetic field producing means (not shown) to rotate within the second receiving portion of the coupling means (42). As rotation of the magnetic field producing means (37) causes changes in magnetic field measured by the magnetic sensor (47), these changes are communicated to the processing system (48), which correlates said changes to a distance travelled by the plunger, and can thereby calculate a selected dose. Now that the desired volume, or projected dose of injectable substance has been selected, the user can commence ejection, and/or injection. This step is illustrated in FIG. 5D, in which one can see the coupling means (42) and plunger head (10) in a position that is distal to their respective positions in FIG. 5C. Moving the coupling means (42) in a distal direction, as illustrated in FIG. 5D, causes the coupling means to push both on the plunger head (10) and the proximal extremity of the shaft (32) to an equal extent. Movement of the shaft (32) in a distal direction, causes the shaft (32) to rotate, and thereby the magnetic field production means (37) to rotate, about the longitudinal axis (25), whereby the magnetic field production means rotates within the second receiving portion of the coupling means. Rotation of the magnetic field production means (37) causes changes in magnetic field measured at the magnetic sensor (47), even though the axial distance between the two is maintained and constant. Further distal movement of the plunger head, via pushing by the user on the coupling means (42) in a distal direction, causes the plunger head (10) to move the plunger to eject, or expel the injectable substance from the syringe body (3). Once the injectable substance has been expelled, FIG. 5E shows a further position of the dose capture device of the invention in which the coupling means has returned to the initial positions of the respective components before use of the device. The plunger head has travelled a certain distance, which has been replicated by the displacement replicator system (30), causing the shaft to be re-housed within the tubular body (23) of the support body (17). In the replicator system (30), the shaft (32) has caused the magnetic field production means (37) to rotate about the longitudinal axis (25) until longitudinal axial translational movement stops, thereby stopping rotational movement of the magnetic producing means (37) about the axis (25). As a result, the processor is capable of processing information from the magnetic sensor (47), which is no longer detecting changes in magnetic field. From this, the processing system is programmed to be able to determine that the injection has been completed, and calculate an ejected dose of injectable substance therefrom, and report the captured dose expelled to an external receiver system, such as a smartphone running a corresponding application or programme for display of such information, via the communications unit included with the processing system.

The invention claimed is:

1. Handheld dose capture device, configured and adapted to be releasably attachable to a handheld injection syringe comprising an elongated body having a longitudinal bore defining a central longitudinal axis, the elongated body having a proximal extremity and a distal extremity, and a syringe plunger located within, and movable along said central longitudinal axis of said bore, the syringe plunger extending beyond said proximal extremity;

wherein the releasably attachable dose capture device comprises: a support body, adapted and configured to be releasably attachable at least one or more locations along a length of the elongated body of the handheld injection syringe, in parallel alignment to the central longitudinal axis of said elongated body;

wherein the support body comprises a tubular body having a longitudinal central bore defining a longitudinal axis that is located parallel to the longitudinal axis of the elongated body of the injection syringe when the dose capture device is mounted on the handheld injection syringe, wherein said support body further includes a mount defining a bore having an internal threaded surface;

a displacement replicator system, adapted and configured to replicate a translational movement of the plunger, in parallel to the longitudinal axis, wherein said displacement replicator system includes a shaft at least partially housed within the central bore of the tubular body and within said bore, said shaft includes an external threading configured to engage, and cooperate with said internal threaded surface of said bore, such that when the shaft is moved in and out of the central bore of the tubular body, engagement between the external threading of the shaft and the internal threaded surface of the bore causes rotational movement of the shaft about the longitudinal axis of the tubular body;

a coupling means, adapted and configured to couple a proximal extremity of the plunger with a proximal extremity of the shaft; and wherein the handheld dose capture device comprises at least one sensor and a processing system, and the at least one sensor and processing system are adapted and configured, when the handheld dose capture device is mounted to the handheld injection syringe, to correlate the rotational movement of the shaft with a selection and/or ejection of a dose of injectable substance operated by a user through the translational movement of the plunger along the longitudinal axis.

2. Handheld dose capture device according to claim 1, wherein the tubular body extends along at least a part of a length of the elongated body of the handheld injection syringe.

3. Handheld dose capture device according to claim 1, wherein the support body comprises a cradle for releasably contacting at least an outer surface of the elongated body of the handheld injection syringe.

4. Handheld dose capture device according to claim 1, wherein the mount is a fixed nut, having an internally threaded bore.

5. Handheld dose capture device according to claim 1, wherein the displacement replicator system further comprises a magnetic field producing means mounted fixed in co-rotation with the shaft, and wherein said sensor is configured to detect changes in magnetic field caused by said rotational movement of the shaft.

6. Handheld dose capture device according to claim 1, wherein the displacement replicator system comprises a magnetic field producing means, and the magnetic field producing means comprises at least one of an annular dipole magnet, a disk-shaped dipole magnet, or at least one pair of diametrally located N-S dipole magnets.

7. Handheld dose capture device according to claim 1, wherein the at least one sensor is a magnetometer.

8. Handheld dose capture device according to claim 1, wherein the at least one sensor is located along the central longitudinal axis of the support body.

9. Handheld dose capture device according to claim 1, wherein the at least one sensor and processing means are housed within the coupling means.

10. Handheld dose capture device according to claim 1, wherein the at least one sensor and processing means are housed within the support body.

11. Handheld dose capture device according to claim 1, wherein the processing system and at least one sensor are in communication one with the other, and the processing system is configured to process signals received from the at least one sensor.

12. Handheld dose capture device according to claim 1, wherein the processing system comprises at least one microcontroller, in electrical communication with at least one of a memory, an autonomous power supply, and a communications unit.

13. Handheld dose capture device according to claim 1, wherein the coupling means comprises a first receiving portion, configured and adapted to receive at least a portion of a plunger head located at the proximal extremity of the plunger.

14. Handheld dose capture device according to claim 1, wherein the coupling means comprises a second receiving portion, configured and adapted to receive at least a portion of a proximal extremity of the displacement means.

15. Handheld dose capture device according to claim 1, wherein the second receiving portion of the coupling means is configured to receive a magnetic field producing means of the displacement replicator system.

16. Handheld dose capture device according to claim 1, wherein the second receiving portion is configured to permit free-rotation of the magnetic field producing means of the displacement replicator system about the longitudinal axis of the support body, within said second receiving portion.

17. Handheld dose capture device according to claim 1, wherein the coupling means comprises:

a first receiving portion, comprising engagement surfaces that snugly surround and engage with at least part of a plunger head to transmit any proximal or distal movement of the coupling means to the plunger head; and a second receiving portion configured to receive and engage with the proximal extremity of a shaft of the displacement replicator system, wherein, when the dose capture device is mounted to the handheld injection syringe, any proximal or distal movement of the plunger head of the handheld injection syringe is transmitted via the coupling means to the proximal extremity of the shaft of the displacement replicator system.

18. Handheld dose capture device according to claim 1, wherein the at least one sensor is an accelerometer configured to detect a positional orientation of the syringe when the dose capture device is mounted thereon, chosen from at least one or more of an injection priming position, a syringe purge position, and an injection ejecting position.

\* \* \* \* \*